(12) United States Patent
Stauber

(10) Patent No.: US 8,377,099 B1
(45) Date of Patent: Feb. 19, 2013

(54) SURGICAL FIXATION SYSTEM AND METHOD

(76) Inventor: Marshall Stauber, Hollywood, FL (US)

( * ) Notice: Subject to any disclaimer, the term of this patent is extended or adjusted under 35 U.S.C. 154(b) by 1196 days.

(21) Appl. No.: 11/698,472

(22) Filed: Jan. 25, 2007

Related U.S. Application Data

(60) Provisional application No. 60/761,813, filed on Jan. 25, 2006.

(51) Int. Cl.
*A61B 17/70* (2006.01)
(52) U.S. Cl. ...................... 606/261; 606/86 A
(58) Field of Classification Search .................. 606/246, 606/250–279, 86 A, 86 B, 86 R, 99
See application file for complete search history.

(56) References Cited

U.S. PATENT DOCUMENTS

| | | | | |
|---|---|---|---|---|
| 4,743,260 | A * | 5/1988 | Burton | 606/279 |
| 6,273,914 | B1 * | 8/2001 | Papas | 623/17.11 |
| 2005/0085813 | A1 * | 4/2005 | Spitler et al. | 606/61 |
| 2006/0200129 | A1 * | 9/2006 | Denti | 606/61 |
| 2006/0212033 | A1 * | 9/2006 | Rothman et al. | 606/61 |

* cited by examiner

*Primary Examiner* — Eduardo C Robert
*Assistant Examiner* — Steven Cotroneo
(74) *Attorney, Agent, or Firm* — McHale & Slavin, P.A.

(57) ABSTRACT

A surgical fixation system comprising at least one pair of elongate members and a plurality of pedicle screws. The elongate members are installed along the length of the spine of the patient. The elongate members are coupled to vertebrae by a set of pedicle screws.

13 Claims, 6 Drawing Sheets

SURGICAL FIXATION SYSTEM AND METHOD

CROSS-REFERENCES TO RELATED APPLICATIONS

The present application is a nonprovisional patent application claiming benefit under 35 U.S.C. §119(e) from U.S. Provisional Application Ser. No. 60/761,813, filed on Jan. 25, 2006, the entire contents of which are hereby expressly incorporated by reference into this disclosure as if set forth fully herein.

BACKGROUND OF THE INVENTION

I. Field of the Invention

The present invention relates to medical devices and methods generally aimed at spinal surgery. In particular, the disclosed system and associated methods related to performing spinal fixation.

II. Discussion of the Prior Art

Fixation systems are often surgically implanted into a patient to aid in the stabilization of a damaged spine or to aid in the correction of other spinal geometric deformities. Spinal fixation systems are often constructed as a framework stabilizing a particular section of the spine. Existing systems often use a combination of rods, plates, pedicle screws and bone hooks for fixing the framework to the affected vertebrae. The configuration required for each patient varies due to the patient's specific anatomical characteristics and ailments. As a result, there is a need for a modular spinal fixation system that allows for a large degree of custom configurations.

The present invention is directed at overcoming, or at least improving upon, the disadvantages of the prior art.

SUMMARY OF THE INVENTION

The present invention accomplishes this goal by providing a system and methods for performing spinal fixation. According to one broad aspect of the present invention, the surgical fixation system comprises at least a pair of single-axis or "fixed" pedicle screw assemblies, a pair of poly-axial pedicle screw assemblies, and a pair of rod members.

Each single-axis and poly-axial pedicle screw assembly of the present invention includes a screw member, a housing, and a locking screw. The screw member includes a shaft. In a single axis pedicle screw assembly, the shaft and housing are integrally formed as a unitary article such that the shaft and housing are in fixed relation (hence the term "single-axis" to describe this type of pedicle screw assembly according to the present invention). In a poly-axial pedicle screw assembly, the shaft and housing are separate articles such that the angle of the housing relative to the screw member may be varied in any number of fashions prior to locking them together (hence the term "poly-axial" to describe this type of pedicle screw assembly according to the present invention). In either assembly, the shaft includes a thread suitable for introduction into and purchase within bone. Each housing includes first and second branches which collectively form a generally "U" shaped area dimensioned to receive at least one of a first end and a second end of the rod member and thereafter the locking screw. In a preferred aspect, each component of the fixed angle pedicle screw assembly and the poly-axial pedicle screw assembly is cannulated such that a K-wire may be used to guide the fixed angle pedicle screw assembly into the patient.

The rod member of the present invention includes a first end and a second end separated by an elongated rod portion. Preferably, the first end, the second end and the elongated rod portion each have a generally circular cross-section, although it is contemplated that the rod member could have any suitable cross-section, including but not limited to generally oval and generally polygonal. According to the present invention, the first end and/or the second end may include a slot for purposes of accommodating a K-wire for guiding the rod member into the patient. The slot is preferably provided as a generally elongate cutout portion extending generally perpendicularly to and diametrically through at least one of the first and second ends such that either end (or both) may be guided directly into the receiving area within the housing of a fixed angle or poly-axial pedicle screw assembly. The rod member of the present invention may be of any length suitable or desirable to connect two or more vertebrae.

As noted above, the fixed and poly-axial pedicle screw assemblies are preferably cannulated (i.e. a longitudinal lumen extends through the locking screws and screw members). As such, each the pedicle screw assemblies of the present invention may be advanced over a K-wire and thereby guided into the patient. This may be preceded by any number of suitable preparatory steps, such as drilling and/or tapping a pilot hole to better accommodate the shafts and/or threads prior to the introduction of screw members.

Once the screw members have been introduced as described above, rod members may thereafter be advanced into the patient for engagement with the pedicle screw assemblies of the present invention. To facilitate this, the rod member may be provided with one or more slots such that at least one of the first and second ends of the rod member may be guided over a K-wire and into a respective housing. Although described herein with the slots positioned at both the first end and the second end of the rod member, it will be appreciated that slots may be provided on one or both ends without departing from the scope of the present invention. Any number of suitable instruments may be employed to facilitate the above-identified step, including but not limited to a pushing or holding device for guiding the rod member into the patient.

After the rod member is introduced as described above, the locking screws may thereafter be introduced and engaged with the housings. It may be preferred to distract the screw members prior to fully locking the locking screws within the housings. In this fashion, the surgeon can ensure that the proper disk height is attained prior to locking the rod members to the pedicle screw assemblies. This screw distraction may be accomplished using any number of suitable instruments. The locking screws may be secured or locked within the respective housing via any number of suitable mechanisms, including but not limited to the manner shown, namely threading the exterior of the locking screws and providing grooves along the interior of the housings. In this fashion, the first end of the rod member will be locked in one housing and the second end will be locked in a second housing. The K-wires may then be withdrawn.

According to an alternative embodiment of the present invention, the rod member may be provided with a ball portion at one end and a rod portion at the other end. The ball portion and/or the rod portion may include any combination of cannulations and/or slots for accommodating a K-wire for guiding the rod member into the patient, such as (by way of example only) a cannulation in the ball portion and a slot in the rod portion. The cannulation is preferably provided as a generally cylindrical lumen extending through the general center of the ball portion such that the center of the ball portion may be guided directly into the receiving area within the housing of one of the fixed angle and/or poly-axial pedicle screw assemblies. The slot is preferably provided as a generally elongate cutout portion extending generally perpendicularly to and diametrically through the rod portion such that the rod portion may be guided directly into the receiving area within the housing of a second of the fixed angle and/or poly-axial pedicle screw assemblies. The rod member of the present invention may be of any length suitable or desirable to connect two or more vertebrae, and may also have a generally circular cross-section, although it is contemplated that the rod portion could have any suitable cross-section, including but not limited to generally oval and generally polygonal.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system and method for performing spinal fixation disclosed herein boasts a variety of inventive features and components that warrant patent protection, both individually and in combination.

Figure 1:
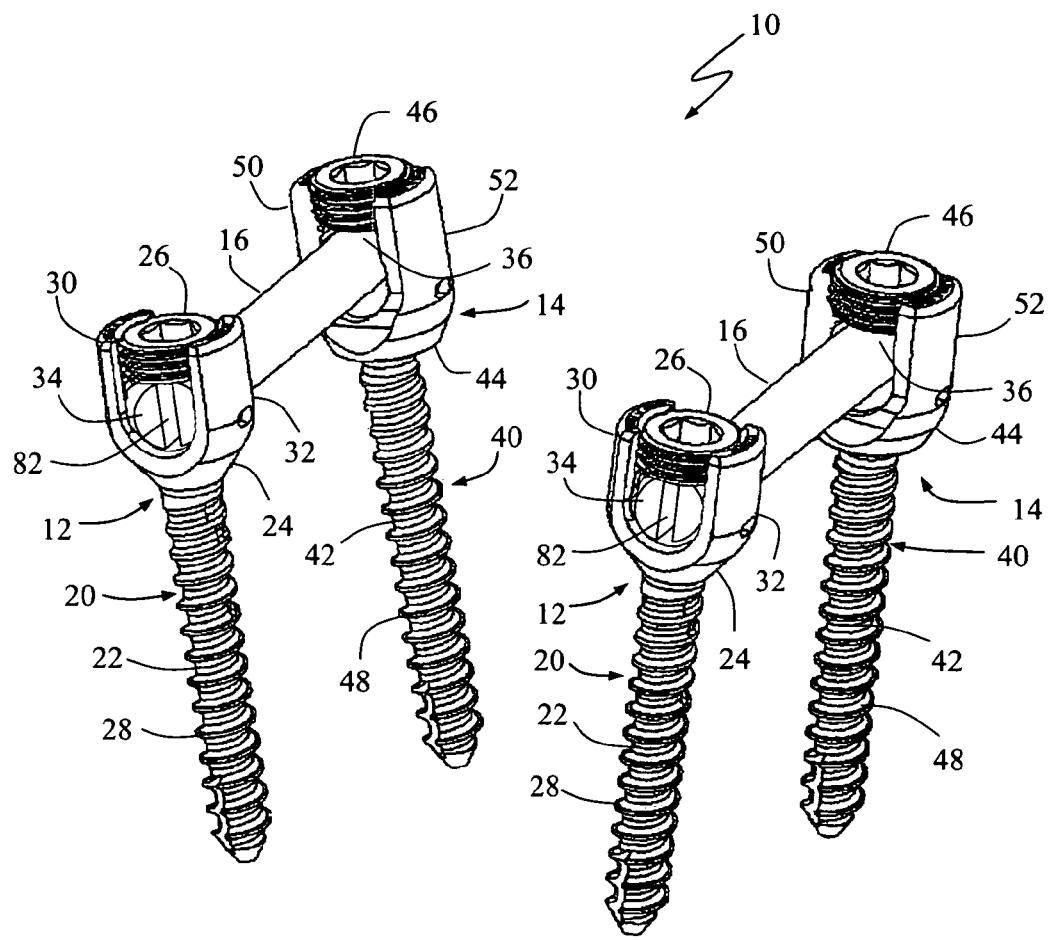
FIG. 1 is a perspective view of a spinal fixation system according to one embodiment of the present invention.

FIG. 1 is a perspective view of a spinal fixation system 10 according to one embodiment of the present invention. The spinal fixation system 10 is suitable for effecting fixation between adjacent vertebral levels within the spine. The spinal fixation system 10 of the present invention as shown in this embodiment includes a pair of single-axis or "fixed" pedicle screw assemblies 12, a pair of poly-axial pedicle screw assemblies 14, and a pair of rod members 16.

The spinal fixation system 10 is shown and described herein as a "single level" fixation system, meaning the single axis pedicle screw assemblies 12 will be fixed into a first vertebral body, the poly-axial pedicle screw assemblies 14 will be fixed to a second vertebral body (adjacent to the first vertebral body), and the rod members 16 will be disposed on either side of (and generally parallel to) the midline of the spine. Although shown and described herein as a "single level" construct, it will be appreciated by those skilled in the art that the spinal fixation system 10 of the present invention may be used in multi-level procedures without departing from the scope of the present invention.

Moreover, before addressing the specifics of each of the single-axis pedicle screw assembly 12, poly-axial pedicle screw assembly 14 and rod member 16, it is to be appreciated that the combination shown in FIG. 1 is set forth by way of example only. That is, the spinal fixation system 10 of the present invention may comprise any number of variations of that shown without departing from the scope of the invention. For example, the spinal fixation system 10 may comprise four (4) of the single-axis pedicle screw assemblies 12, four (4) of the poly-axial pedicle screw assemblies 14, and/or any combination of single and poly-axial pedicle screw assemblies 12, 14, in conjunction with the rod members 16 to effect spinal fixation.

Each single-axis pedicle screw assembly 12 of the present invention includes a screw member 20 having a shaft 22 and a housing 24, as well as a locking screw 26. The shaft 22 and housing 24 are integrally formed as a unitary article such that the shaft 22 and housing 24 are in fixed relation, hence the term "single-axis" to describe this type of pedicle screw assembly 12 according to the present invention. The shaft 22 includes a thread 28 suitable for introduction into and purchase within bone. Each housing 24 includes first and second branches 30, 32 which collectively form a generally "U" shaped area dimensioned to receive at least one of a first end 34 and a second end 36 of the rod member 16 and thereafter the locking screw 26. In a preferred aspect, each component of the fixed angle pedicle screw assembly 12 is cannulated (i.e. it is equipped with a longitudinally lumen extending through the locking screw 26 and screw member 20) such that a K-wire may be used to guide the fixed angle pedicle screw assembly 12 into the patient.

Each poly-axial pedicle screw assembly 14 of the present invention includes a screw member 40, a housing 44, and a locking screw 46. The screw member 40 includes a shaft 42. The screw member 40 and housing 44 are separate articles such that the angle of the housing 44 relative to the screw member 40 may be varied in any number of fashions prior to locking them together, hence the term "poly-axial" to describe this type of pedicle screw assembly 14 according to the present invention. The shaft 42 includes a thread 48 suitable for introduction into and purchase within bone. Each housing 44 includes first and second branches 50, 52, which collectively form a generally "U" shaped area dimensioned to receive at least one of a first end 34 and a second end 36 of the rod member 16 and thereafter the locking screw 46. In a preferred aspect, each component of the poly-axial pedicle screw assembly 14 is cannulated (i.e. it is equipped with a longitudinal lumen extends through the locking screw 46 and screw member 40) such that a K-wire may be used to guide the poly-axial pedicle screw assembly 14 into the patient.

Figure 2:
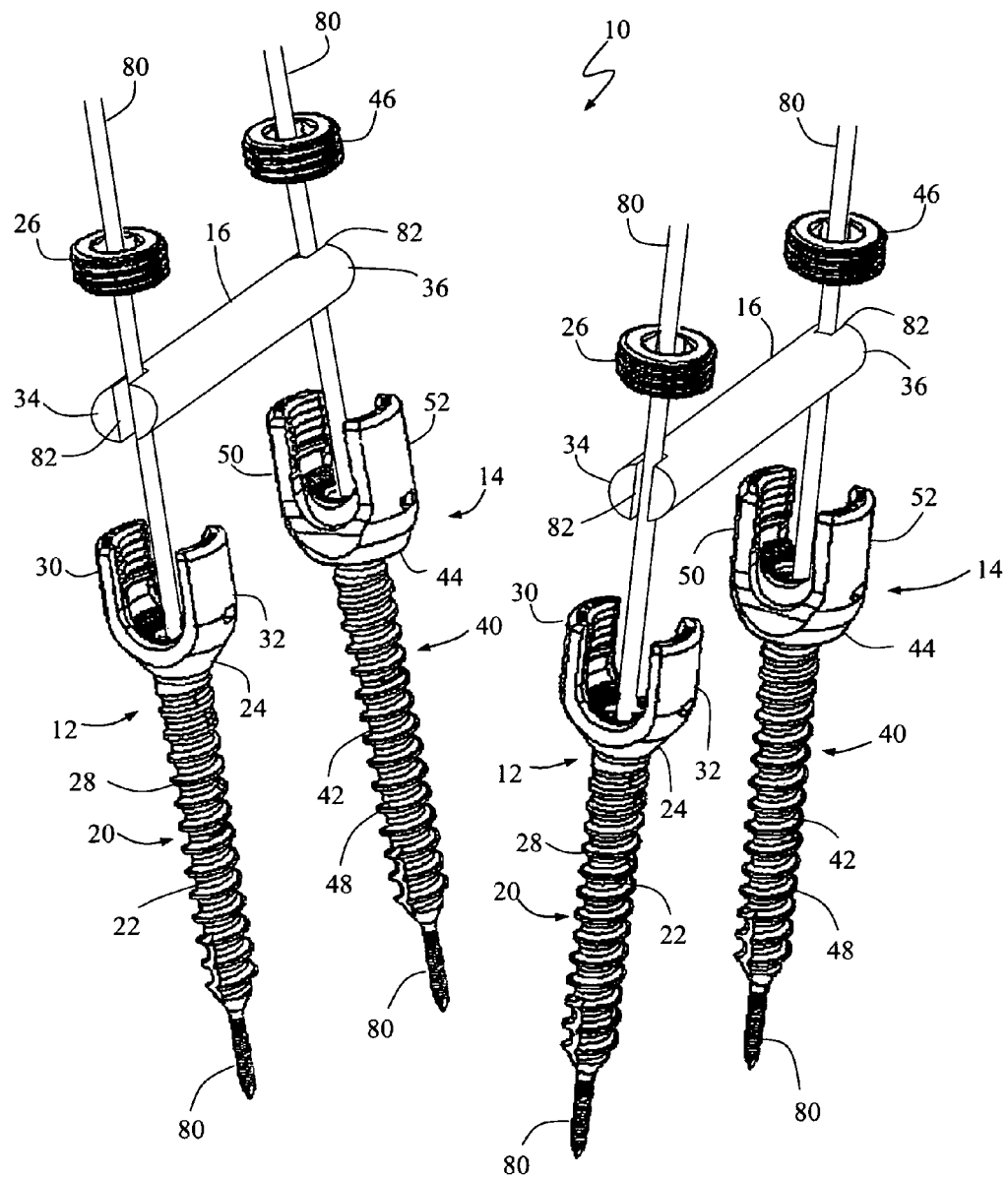
FIG. 2 is an exploded perspective view of the spinal fixation system of FIG. 1, illustrating a method of implanting the pedicle screws and rod member.

FIG. 2 illustrates a method of using the spinal fixation system 10 according to one embodiment of the present invention. As noted above, the fixed and poly-axial pedicle screw assemblies 12, 14 are preferably cannulated (i.e. a longitudinal lumen extends through the locking screws 26, 46 and screw members 20, 40, respectively). As such, each the pedicle screw assemblies 12, 14 of the present invention may be advanced over a K-wire 80 and thereby guided into the patient. More specifically, the K-wires 80 may be used (with or without image guidance, such as X-ray and/or fluoroscopy systems) to target the location and trajectory to introduce the shafts 22, 42 of the screw members 20, 40, respectively, into the pedicle of interest. Once the desired location and trajectory are identified, the screw members 20, 40 may be advanced over a respective K-wire 80 until the distal end of the shafts 22, 42 contact the pedicle, after which point the screw members 20, 40 may be rotated about the K-wire 80 (e.g., by rotating the housings 24, 44 via any suitable instrumentation) until the shafts 22, 42 are introduced a desired depth into the pedicle and/or vertebral body. This may be preceded by any number of suitable preparatory steps, such as drilling and/or tapping a pilot hole to better accommodate the shafts 22, 42 and/or threads 28, 48 prior to the introduction of screw members 20, 40.

Once the screw members 20, 40 have been introduced as described above, rod members 16 may thereafter be advanced into the patient for engagement with the pedicle screw assemblies 12, 14 of the present invention. To facilitate this, the rod member 16 may be provided with one or more slots 82 such that at least one of the first and second ends 34, 36 of the rod member 16 may be guided over a K-wire 80 and into a respective housing 24, 44. Although described herein with the slots 82 positioned at both the first end 34 and the second end 36 of the rod member 16, it will be appreciated that slots 82 may be provided on one or both ends 34, 36 without departing from the scope of the present invention. Any number of suitable instruments may be employed to facilitate the above-identified step, including but not limited to a pushing or holding device for guiding the rod member 16 into the patient.

After the rod member 16 is introduced as described above, the locking screws 26, 46 may thereafter be introduced and engaged with the housings 24, 44. It may be preferred to distract the screw members 20, 40 prior to fully locking the locking screws 26, 46 within the housings 24, 44. In this fashion, the surgeon can ensure that the proper disk height is attained prior to locking the rod members 16 to the pedicle screw assemblies 12, 14. This screw distraction may be accomplished using any number of suitable instruments. The locking screws 26, 46 may be secured or locked within the respective housing 24, 44 via any number of suitable mechanisms, including but not limited to the manner shown, namely threading the exterior of the locking screws 26, 46 and providing grooves along the interior of the housings 24, 44.

The spinal fixation system 10 of the present invention is suitable for both open and/or percutaneous procedures. In an open procedure, any or all of the components of the pedicle screw systems 12, 14 and rod member 16 may be introduced without the assistance of a K-wire (and, for that matter, such components may be non-cannulated). During a percutaneous procedure, however, both the pedicle screw assemblies 12, 14 and rod member 16 may be introduced percutaneously through the use of K-wire guidance. According to one embodiment, this may be accomplished by percutaneously (i.e. using a K-wire for guidance) introducing a first fixed pedicle screw assembly 12 into a first vertebral body, introducing a first poly-axial pedicle screw assembly 14 in an adjacent vertebral body, creating an incision extending between and down to the first fixed and poly-axial pedicle screw assemblies 12, 14, introducing the rod member 16 into the housings 24, 44, respectively, (optionally distracting), and introducing the locking screws 26, 46 to lock the rod member 16 relative to the pedicle screw assemblies 12, 14. In this fashion, the first end 34 of the rod member 16 will be locked in the housing 24 and the second end 36 will be locked in the housing 44. The K-wires 80 may then be withdrawn. Any number of suitable instruments may be employed to facilitate the above-identified steps, including but not limited to a screwdriver for screwing the locking screws 26, 46 into the housings 24, 44. In either event (open or percutaneous introduction), once implanted the spinal fixation system 10 of the present invention will appear as shown in FIG. 1.

Figure 3:
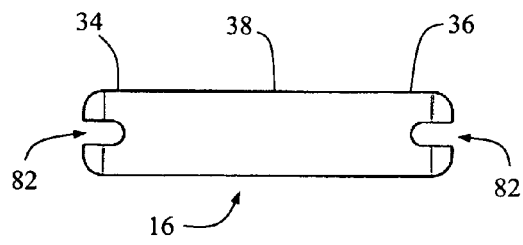
FIG. 3 is a top plan view of a rod member according to one embodiment of the present invention.
Figure 4:
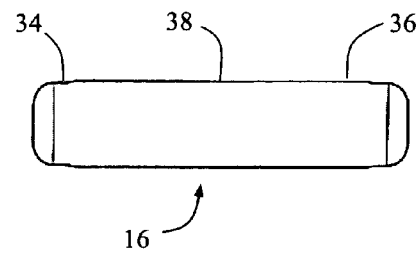
FIG. 4 is a plan view of the rod member of FIG. 3 rotated 90°.
Figure 5:
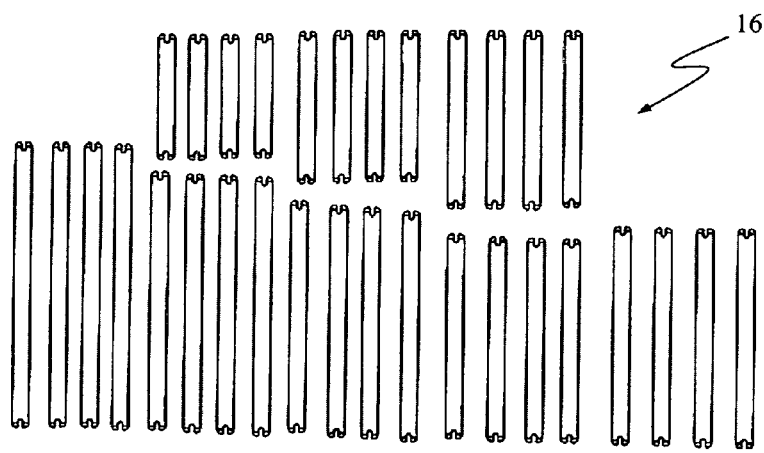
FIG. 5 is a top plan view of an assortment of rod members according to one embodiment of the present invention.

The rod member 16 will now be described in detail with reference to FIGS. 3-5. As set forth above, the rod member 16 of the present invention includes a first end 34 and a second end 36 separated by an elongated rod portion 38. Preferably, the first end 34, the second end 36 and the elongated rod portion 38 each have a generally circular cross-section, although it is contemplated that the rod member could have any suitable cross-section, including but not limited to generally oval and generally polygonal. According to the present invention, the first end 34 and/or the second end 36 may include a slot 82 for purposes of accommodating a K-wire for guiding the rod member 16 into the patient. The slot 82 is preferably provided as a generally elongate cutout portion extending generally perpendicularly to and diametrically through at least one of the first and second ends 34, 36 such that either end 34, 36 (or both) may be guided directly into the receiving area within the housing 24 (and/or housing 44). The slot 82 is provided with a generally elongated shape to accommodate variations in the distance between the housing 24 and housing 44, which may exist due to surgeon placement or other factors. The rod member 16 of the present invention may be of any length suitable or desirable to connect two or more vertebrae, and may be generally provided in a range of 25-300 mm. By way of example only, FIG. 5 shows a plurality of rod members 16 having a variety of lengths as contemplated by the present invention.

Figure 6:
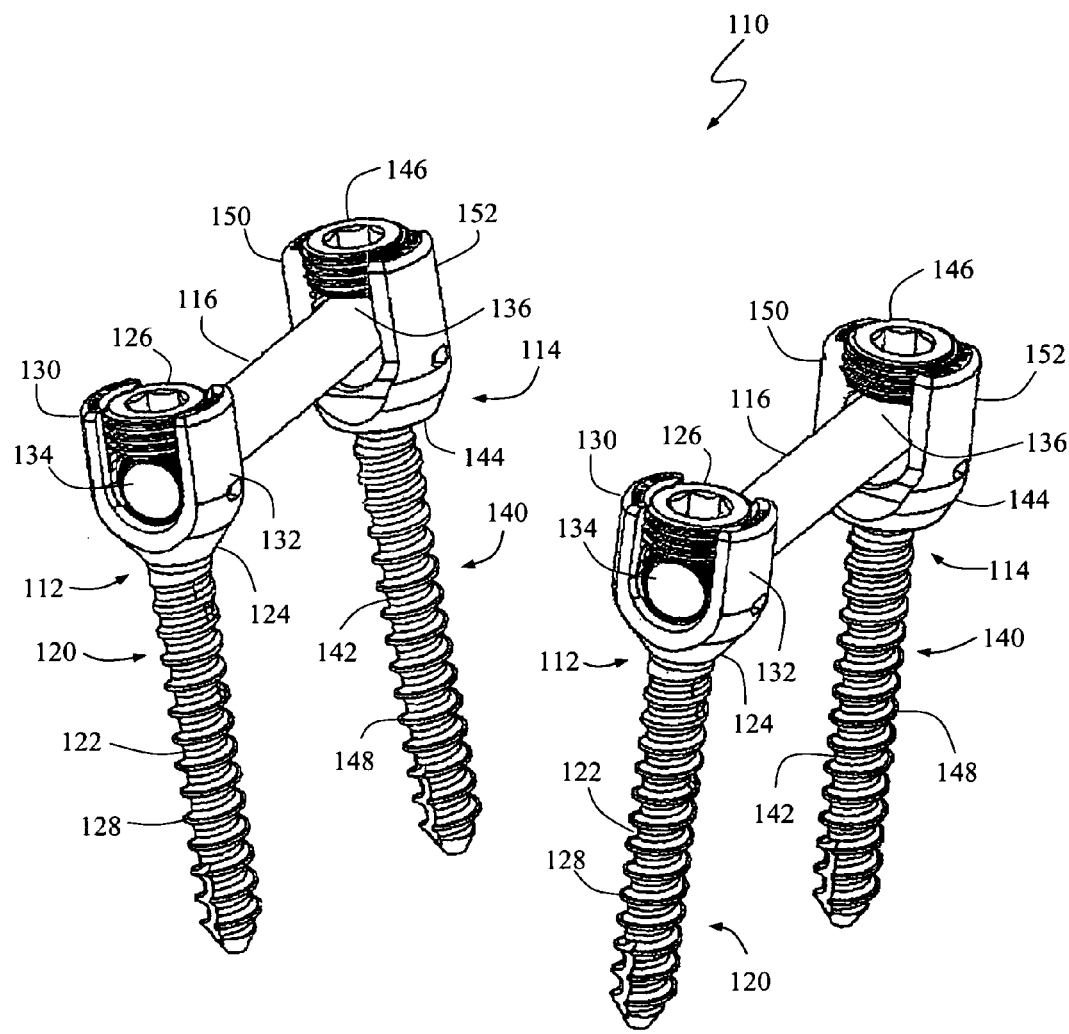
FIG. 6 is a perspective view of a spinal fixation system according to an alternative embodiment of the present invention.

FIG. 6 is a perspective view of a spinal fixation system 110 according to an alternative embodiment of the present invention. The spinal fixation system 110 is suitable for effecting fixation between adjacent vertebral levels within the spine. The spinal fixation system 110 of the present invention as shown in this embodiment includes a pair of single-axis or "fixed" pedicle screw assemblies 112, a pair of poly-axial pedicle screw assemblies 114, and a pair of rod members 116.

As with the spinal fixation system 10 discussed above, the spinal fixation system 110 is shown and described herein as a "single level" fixation system, meaning the single axis pedicle screw assemblies 112 will be fixed into a first vertebral body, the poly-axial pedicle screw assemblies 114 will be fixed to a second vertebral body (adjacent to the first vertebral body), and the rod members 116 will be disposed on either side of (and generally parallel to) the midline of the spine. Although shown and described herein as a "single level" construct, it will be appreciated by those skilled in the art that the spinal fixation system 110 of the present invention may be used in multi-level procedures without departing from the scope of the present invention.

Moreover, before addressing the specifics of each of the single-axis pedicle screw assembly 112, poly-axial pedicle screw assembly 114 and rod member 116, it is to be appreciated that the combination shown in FIG. 6 is set forth by way of example only. That is, the spinal fixation system 110 of the present invention may comprise any number of variations of that shown without departing from the scope of the invention. For example, the spinal fixation system 110 may comprise four (4) of the single-axis pedicle screw assemblies 112, four (4) of the poly-axial pedicle screw assemblies 14, and/or any combination of single and poly-axial pedicle screw assemblies 112, 114, in conjunction with the rod members 116 to effect spinal fixation.

Each single-axis pedicle screw assembly 112 of the present invention includes a screw member 120 having a shaft 122 and a housing 124, as well as a locking screw 126. The shaft 122 and housing 124 are integrally formed as a unitary article such that the shaft 122 and housing 124 are in fixed relation, hence the term "single-axis" to describe this type of pedicle screw assembly 112 according to the present invention. The shaft 122 includes a thread 128 suitable for introduction into and purchase within bone. Each housing 124 includes first and second branches 130, 132 which collectively form a generally "U" shaped area dimensioned to receive at least one of a ball portion 134 and/or a rod portion 136 (forming either end of the rod member 116 according to a further aspect of the present invention) and thereafter the locking screw 126.

In a preferred aspect, each component of the fixed angle pedicle screw assembly 112 is cannulated (i.e. it is equipped with a longitudinally lumen extending through the locking screw 126 and screw member 120) such that a K-wire may be used to guide the fixed angle pedicle screw assembly 112 into the patient.

Each poly-axial pedicle screw assembly 114 of the present invention includes a screw member 140, a housing 144, and a locking screw 146. The screw member 140 includes a shaft 142. The screw member 140 and housing 144 are separate articles such that the angle of the housing 144 relative to the screw member 140 may be varied in any number of fashions prior to locking them together, hence the term "poly-axial" to describe this type of pedicle screw assembly 114 according to the present invention. The shaft 142 includes a thread 148 suitable for introduction into and purchase within bone. Each housing 144 includes first and second branches 150, 152, which collectively form a generally "U" shaped area dimensioned to receive at least one of a ball portion 134 and/or a rod portion 136 (forming either end of the rod member 116 according to a further aspect of the present invention) and thereafter the locking screw 146.

In a preferred aspect, each component of the poly-axial pedicle screw assembly 114 is cannulated (i.e. it is equipped with a longitudinal lumen extends through the locking screw 146 and screw member 140) such that a K-wire may be used to guide the poly-axial pedicle screw assembly 114 into the patient.

Figure 7:
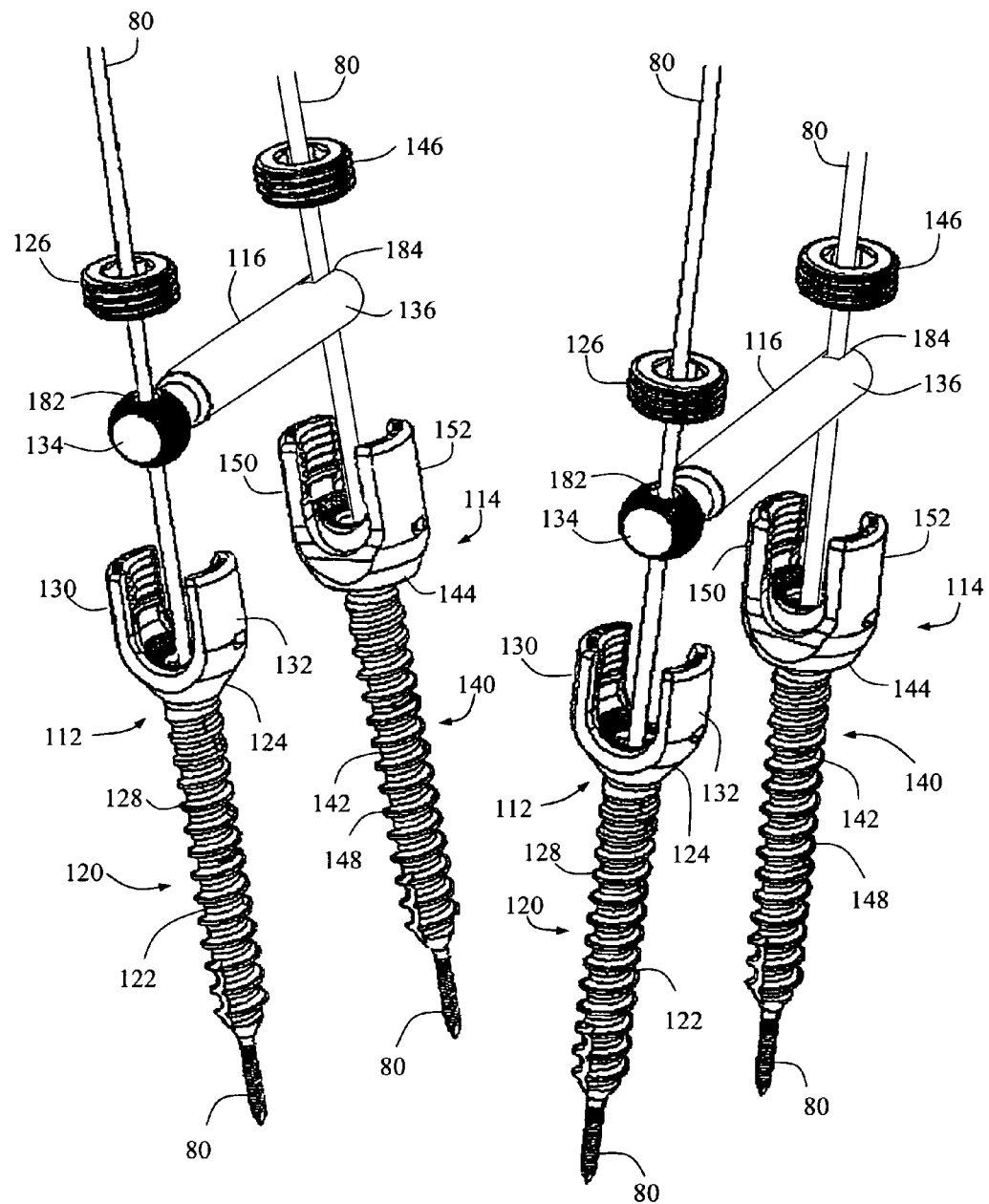
FIG. 7 is an exploded perspective view of the spinal fixation system of FIG. 6, illustrating a method of implanting the pedicle screws and rod member.
Figure 8:
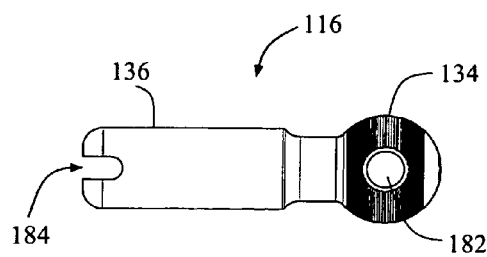
FIG. 8 is a top plan view of a rod member according to an alternative embodiment of the present invention.
Figure 9:
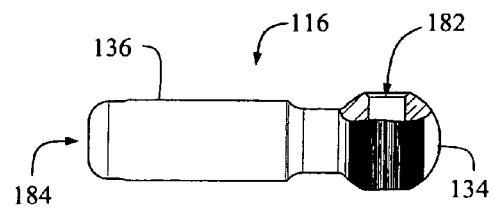
FIG. 9 is a plan view of the rod member of FIG. 8 rotated 90° with a portion cut away.
Figure 10:
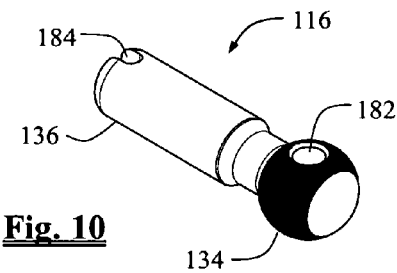
FIG. 10 is a perspective view of the rod member of FIG. 8.

FIG. 7 illustrates a method of using the spinal fixation system 110 according to one embodiment of the present invention. As noted above, the fixed and poly-axial pedicle screw assemblies 112, 114 are preferably cannulated (i.e. a longitudinal lumen extends through the locking screws 126, 146 and screw members 120, 140, respectively). As such, each the pedicle screw assemblies 112, 114 of the present invention may be advanced over a K-wire 80 and thereby guided into the patient. More specifically, the K-wires 80 may be used (with or without image guidance, such as X-ray and/or fluoroscopy systems) to target the location and trajectory to introduce the shafts 122, 142 of the screw members 120, 140, respectively, into the pedicle of interest. Once the desired location and trajectory are identified, the screw members 120, 140 may be advanced over a respective K-wire 80 until the distal end of the shafts 122, 142 contact the pedicle, after which point the screw members 120, 140 may be rotated about the K-wire 80 (e.g., by rotating the housings 124, 144 via any suitable instrumentation) until the shafts 122, 142 are introduced a desired depth into the pedicle and/or vertebral body. This may be preceded by any number of suitable preparatory steps, such as drilling and/or tapping a pilot hole to better accommodate the shafts 122, 142 and/or threads 128, 148 prior to the introduction of screw members 120, 140.

Once the screw members 120, 140 have been introduced as described above, rod members 116 may thereafter be advanced into the patient for engagement with the pedicle screw assemblies 112, 114 of the present invention. To facilitate this, the rod member 116 may be provided with one or more cannulations and/or slots (e.g. cannulation 182 in the ball portion 134 and/or slot 184 in the rod portion 136) such that one or more ends of the rod member 116 may be guided over a K-wire 80 and into a respective housing 124, 144. Although described herein with the ball portion 134 engaging within the housing 124 of the fixed angle pedicle screw assemblies 112 and the rod portion 136 engaging within the housing 144 of the poly-axial pedicle screw assembly 114, it will be appreciated that this may be reversed in one or both sides without departing from the scope of the present invention. Any number of suitable instruments may be employed to facilitate the above-identified step, including but not limited to a pushing or holding device for guiding the rod member 116 into the patient.

After the rod member 116 is introduced as described above, the locking screws 126, 146 may thereafter be introduced and engaged with the housings 124, 144. It may be desirable to adjust the position of the rod member 116 relative to the pedicle screw assemblies 112, 114 according to a still further aspect of the present invention. More specifically, the spherical nature of the ball region 134 of the rod member 116 will (prior to locking) allow it to rotate within the housing 124. As such, the ball region 134 will be loosely disposed within the housing 124 such that the remainder of the rod member 116 may be angled therefrom in any number of desired manners (e.g. up, down, side-to-side and/or any variation thereof) depending upon the situation and need. This may advantageously facilitate positioning the rod region 136 into the housing 144 after the ball region 134 has already been positioned within housing 124. Moreover, this may reduce if not eliminate the need to bend the rod member 116 as with traditional rod members of prior art pedicle screw systems.

It may be preferred to distract the screw members 120, 140 prior to fully locking the locking screws 126, 146 within the housings 124, 144. In this fashion, the surgeon can ensure that the proper disk height is attained prior to locking the rod members 116 to the pedicle screw assemblies 112, 114. This screw distraction may be accomplished using any number of suitable instruments. The locking screws 126, 146 may be secured or locked within the respective housing 124, 144 via any number of suitable mechanisms, including but not limited to the manner shown, namely threading the exterior of the locking screws 126, 146 and providing grooves along the interior of the housings 124, 144.

The spinal fixation system 110 of the present invention is suitable for both open and/or percutaneous procedures. In an open procedure, any or all of the components of the pedicle screw systems 112, 114 and rod member 116 may be introduced without the assistance of a K-wire (and, for that matter, such components may be non-cannulated). During a percutaneous procedure, however, both the pedicle screw assemblies 112, 114 and rod member 116 may be introduced percutaneously through the use of K-wire guidance. According to one embodiment, this may be accomplished by percutaneously (i.e. using a K-wire for guidance) introducing a first fixed pedicle screw assembly 112 into a first vertebral body, introducing a first poly-axial pedicle screw assembly 114 in an adjacent vertebral body, creating an incision extending between and down to the first fixed and poly-axial pedicle screw assemblies 112, 114, introducing the rod member 116 into the housings 124, 144, respectively, (optionally distracting), and introducing the locking screws 126, 146 to lock the rod member 116 relative to the pedicle screw assemblies 112, 114. In this fashion, the ball portion 134 of the rod member 116 will be locked in the housing 124 and the rod portion 136 will be locked in the housing 144. The K-wires 80 may then be withdrawn. Any number of suitable instruments may be employed to facilitate the above-identified steps, including but not limited to a screwdriver for screwing the locking screws 126, 146 into the housings 124, 144. In either event (open or percutaneous introduction), once implanted the spinal fixation system 110 of the present invention will appear as shown in FIG. 6.

Figure 11:
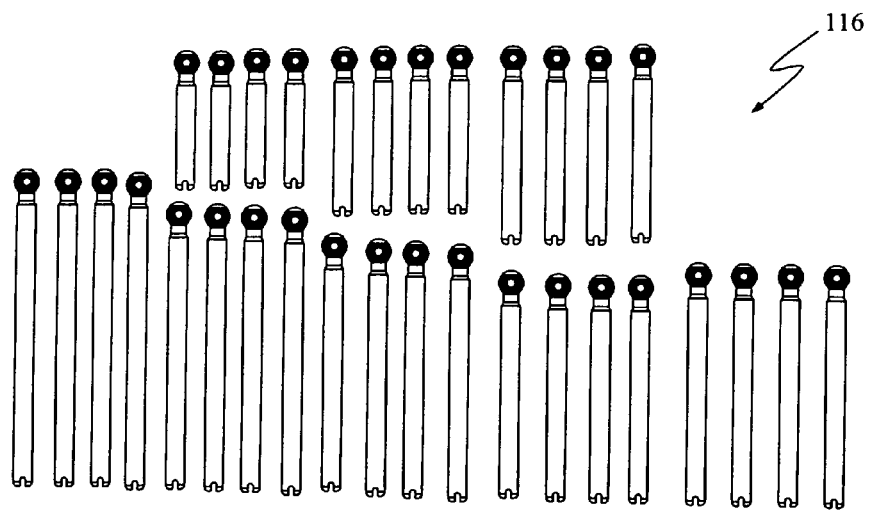
FIG. 11 is a top plan view of an assortment of rod members according to an alternative embodiment the present invention.

The rod member 116 will now be described in detail with reference to FIGS. 8-11. As set forth above, the rod member 116 of the present invention includes a ball portion 134 at one end and a rod portion 136 at the other end. According to the present invention, the ball portion 134 and/or the rod portion 136 may include cannulations and/or slots for accommodating a K-wire for guiding the rod member 116 into the patient, such as represented by cannulation 182 (in ball portion 134) and slot 184 (in rod portion 136). The cannulation 182 is preferably provided as a generally cylindrical lumen extending through the general center of the ball portion 134 such that the center of the ball portion 134 may be guided directly into the spherical receiving area within the housing 124 (or housing 144 if the rod member 116 is reversed). The slot 184 is preferably provided as a generally elongate cutout portion extending generally perpendicularly to and diametrically through the rod portion 136 such that the rod portion 136 may be guided directly into the receiving area within the housing 144 (or housing 124 if the rod member 116 is reversed). The slot 184 is provided with a generally elongated shape to accommodate variations in the distance between the housing 124 and housing 144, which may exist due to surgeon placement or other factors. The rod member 116 of the present invention may be of any length suitable or desirable to connect two or more vertebrae, and may be generally provided in a range of 25-300 mm. By way of example only, FIG. 11 shows a plurality of rod members 116 having a variety of lengths as contemplated by the present invention. Preferably, the rod portion 136 has a generally circular cross-section, although it is contemplated that the rod portion 136 could have any suitable cross-section, including but not limited to generally oval and generally polygonal.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

The invention claimed is:

1. A system for performing spinal fusion, comprising:
    a first K-wire extending into a first vertebral body;
    a second K-wire extending into a second vertebral body;
    a first screw comprising a first housing portion and a first anchor portion, said first anchor portion dimensioned to provide purchase into a first vertebral body, said first screw operatively engaging said first K-wire,
    a second screw comprising a second housing portion and a second anchor portion, said second anchor portion dimensioned to provide purchase into a second vertebral body, said second screw operatively engaging said second K-wire;
    a rigid elongate body having a first end, a second end, and a longitudinal axis, said first end being located at one end of said elongate body and dimensioned to engage said first housing portion, said second end being located at an opposite end of said elongate body and dimensioned to engage said second housing portion, said first end of said elongate body having a face, said face extending substantially orthogonal to said longitudinal axis of said elongate body, said face also extending substantially parallel to a cross section of said elongate body; and
    a slot extending across said face of at least said first end and operatively engaging said first K-wire or said second K-wire.

2. The system of claim 1, wherein said rigid, elongated body includes a length dimension that is sufficient to span between a first vertebral body and a second vertebral body.

3. The system of claim 1, wherein said second end includes a slot extending across a face of said second end and being dimensioned to slidably engage a K-wire.

4. The system of claim 1, wherein said second end includes a slot extending therethrough.

5. The system of claim 1, including a substantially spherical ball portion located at an end of said stabilization rod opposite said at least first end which includes said slot, said substantially spherical ball includes a passageway therethrough dimensioned to slidably receive a K-wire.

6. The system of claim 5, wherein said first screw comprises at least one of a polyaxial and a fixed angle screw.

7. The system of claim 5, wherein said second screw comprises at least one of a polyaxial and a fixed angle screw.

8. The system of claim 5, wherein said first vertebral body is adjacent to said second vertebral body.

9. A method for performing spinal fusion surgery, comprising:
    inserting a first K-wire into a first vertebral body;
    inserting a second K-wire into a second vertebral body;
    inserting a first screw onto said first K-wire and into said first vertebral body, said first screw comprising a first housing portion and a first anchor portion, said first anchor portion dimensioned to provide purchase into said first vertebral body;
    inserting a second screw onto said second K-wire and into said second vertebral body, said second screw comprising a second housing portion and a second anchor portion, said second anchor portion dimensioned to provide purchase into said second vertebral body; and
    advancing a rigid elongate body having a first end, a second end, and a longitudinal axis, said first end being located at one end of said elongate body and said second end being located at an opposite end of said elongate body, said first end of said elongate body having a face, said face extending substantially orthogonal to said longitudinal axis of said elongate body, said face also extending substantially parallel to a cross section of said elongate body;
    a slot extending across said face of at least said first end, said slot slidably engaging said first or said second K-wire; and
    said first end engaging said first housing portion and said second end engaging said second housing portion.

10. The method of claim 9, including a substantially spherical ball portion located at an end of said elongate rod opposite said at least first end which includes said slot, said substantially spherical ball includes a passageway therethrough slidably receiving said first or said second K-wire.

11. The method of claim 10, wherein said first screw comprises at least one of a polyaxial and a fixed angle screw.

12. The method of claim 10, wherein said second screw comprises at least one of a polyaxial and a fixed angle screw.

13. The method of claim 10, wherein said first vertebral body is adjacent to said second vertebral body.

* * * * *